United States Patent
Kumar et al.

(10) Patent No.: US 9,254,352 B2
(45) Date of Patent: Feb. 9, 2016

(54) FLUID FILTERING DEVICE AND METHOD

(76) Inventors: Rajen Nirwal Kumar, Troy, MI (US);
Caitlin O'Brien Winget, Shelburne, VT (US); Theresa Kate Fisher, Ann Arbor, MI (US); Alexander Hobbes Harrington, Ann Arbor, MI (US); Aliaksandra Kapshai, Ypsilanti, MI (US); Gillian Elizabeth Henker, Glenshaw, PA (US)

(*) Notice: Subject to any disclaimer, the term of this patent is extended or adjusted under 35 U.S.C. 154(b) by 808 days.

(21) Appl. No.: 13/445,837

(22) Filed: Apr. 12, 2012

(65) Prior Publication Data
US 2013/0270161 A1  Oct. 17, 2013

(51) Int. Cl.
| B01D 35/02 | (2006.01) |
| A61M 1/00 | (2006.01) |
| B01D 35/30 | (2006.01) |
| B01D 29/92 | (2006.01) |

(52) U.S. Cl.
CPC ........... *A61M 1/0005* (2013.01); *A61M 1/0056* (2013.01); *B01D 29/925* (2013.01); *B01D 35/02* (2013.01); *B01D 35/30* (2013.01)

(58) Field of Classification Search
None
See application file for complete search history.

(56) References Cited

U.S. PATENT DOCUMENTS

| 472,547 | A | * | 4/1892 | Robertson | .................. | 210/416.3 |
| 2,436,077 | A | * | 2/1948 | Robertson | ..................... | 210/317 |

FOREIGN PATENT DOCUMENTS

DE  3533936 A1 * 3/1987

* cited by examiner

*Primary Examiner* — Terry Cecil
(74) *Attorney, Agent, or Firm* — Hudak Consulting Group LLC

(57) ABSTRACT

An apparatus including a hollow body, an inlet fluidly coupled to the hollow body, a piston slidably engaged within the hollow body, and a filter arranged within the hollow body between the inlet and piston. The piston and hollow body cooperatively generate a negative pressure, relative to ambient, within the hollow body during piston translation from a first position, proximal the inlet, to a second position, distal the inlet, to draw a fluid, such as blood, through the filter into the hollow body. The piston and hollow body cooperatively generate a positive pressure, relative to ambient, within the hollow body during piston translation from the second position to the first position to egress the filtered fluid from the hollow body.

20 Claims, 4 Drawing Sheets

FLUID FILTERING DEVICE AND METHOD

TECHNICAL FIELD

This invention relates generally to the medical device field, and more specifically to a new and useful blood filtering device in the medical device field.

BACKGROUND

Autologous blood transfusion is a process that removes a patient's own blood to later be re-transfused into their body. In developing countries, a manual blood transfusion technique is commonly used due to the small quantities and high cost of donated blood available. Currently, manual blood transfusion includes collecting blood from an open wound or off a collection surface, manually removing large blood clots, filtering the blood though gauze pads to remove smaller blood clots, and introducing the filtered blood into a storage bag, where the blood is mixed with an anticoagulant solution and stored until the blood can be transferred back into the patient. This process is very labor, material and time intensive, often involving the coordination of 3-4 trained personnel. Furthermore, this process can suffer from sterility issues. Thus, there is a need in the medical device field to create a new and useful blood transfusion device.

DESCRIPTION OF THE PREFERRED EMBODIMENTS

The following description of the preferred embodiments of the invention is not intended to limit the invention to these preferred embodiments, but rather to enable any person skilled in the art to make and use this invention.

Figure 1:
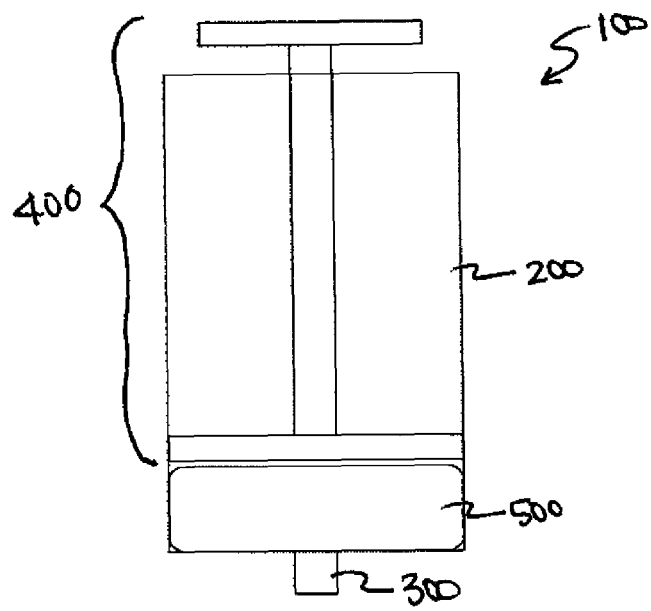
FIG. 1 is a schematic representation of the apparatus.

As shown in FIG. 1, the apparatus 100 for filtering blood includes a hollow body 200, an inlet 300 fluidly coupled to the hollow body 200, a piston 400 slidably disposed within the hollow body 200, and a filter module 500 removably coupled within the hollow body 200. The filter module 500 and piston 400 are arranged within the hollow body 200 such that the filter module 500 is located between the inlet 300 and the piston 400. The apparatus can additionally and/or alternatively include a body valve 220 that controls fluid flow between the inlet 300 and hollow body 200, an outlet 240 that allows fluid egress from the hollow body 200 without passing through the contaminated filter, a reservoir 320 fluidly coupling the inlet 300 to the hollow body 200, and an inlet coupling mechanism 340 that removably couples the inlet 300 to the hollow body 200. The apparatus preferably functions to filter, store and/or transport blood. For example, the apparatus can be used in blood transfusions, wherein the apparatus is used to filter blood drawn from a patient or from a collection volume, such as a bowl or a floor. The apparatus preferably removes blood clots from the blood, and can additionally filter foreign particulates from the blood. The apparatus is preferably passive and manually operated by a user, but can alternatively be active and driven by an electronic system.

Figure 2:
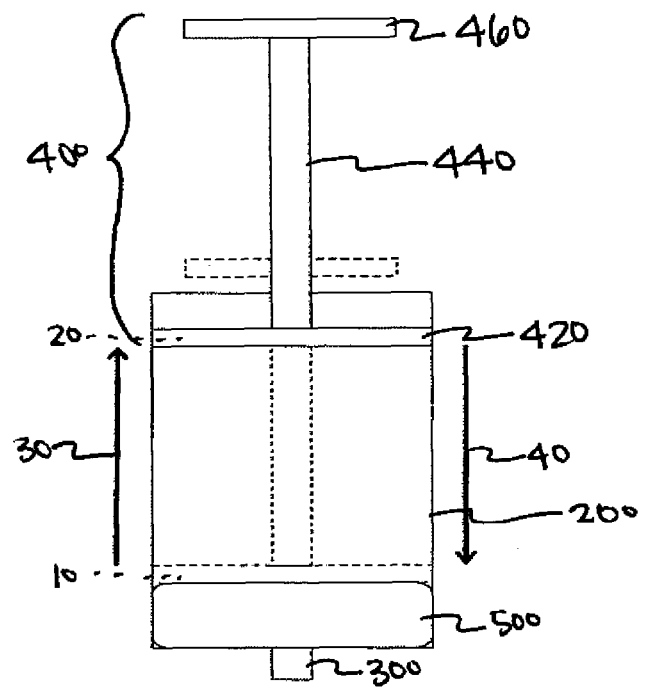
FIG. 2 is a schematic representation of the apparatus between the intake stroke and the compression stroke.

As shown in FIG. 2, the apparatus is preferably operational between an intake stroke 30 and a compression stroke 40. During the intake stroke 30, the piston 400, more preferably the piston head 420, moves from a first position 10, proximal the inlet 300, to a second position 20, distal the inlet 300. During the intake stroke 30, the piston 400 and hollow body 200 cooperatively generate a negative pressure within the hollow body 200 relative to ambient. In other words, the piston 400 applies a suction force to the hollow body interior that draws fluid into the hollow body 200. During the compression stroke 40, the piston head 420 moves from the second position 20 to the first inlet 300. During the compression stroke 40, the piston 400 and hollow body 200 cooperatively generate a positive pressure within the hollow body 200 relative to ambient. In other words, the piston 400 applies an expulsion force to the hollow body interior that expels fluid from the hollow body 200. The hollow body 200, piston head 420, and body valve 220 preferably cooperatively define a hollow body volume that expands as the piston 400 moves through the intake stroke 30, and contracts as the piston 400 moves through the compression stroke 40. The filtered fluid, more preferably filtered blood, preferably occupies the hollow body volume.

The apparatus is preferably configured to minimize clotting as the blood is drawn into the hollow body 200. The apparatus preferably minimizes clotting by controlling the blood flow rate into and out of the apparatus. The apparatus allows for a blood flow rate of at least 0.5 L/min to 1.6 L/min. However, the apparatus can facilitate a higher or lower blood flow rate. In one variation, the apparatus controls the blood flow rate by controlling the maximum negative pressure (e.g. by controlling the inlet 300 to hollow body 200 cross sectional ratio). In one alternative, the apparatus is configured such that the maximum negative pressure does not exceed 150 mm Hg (below ambient pressure/atmospheric pressure) during the intake stroke. In another variation, the blood flow rate is controlled by the inlet 300 shape. In another variation, the blood flow rate is controlled by controlling the rate at which the piston 400 is moved through the hollow body 200 (e.g. by controlling the friction force applied by the piston head 420 against the hollow body 200 walls). However, any other suitable means or method of controlling the blood flow rate can be included.

As shown in FIG. 1, the hollow body 200 of the apparatus functions to cooperatively generate a positive and/or negative pressure with the piston 400, and also functions to hold ingressed fluid. The hollow body 200 can additionally function to retain the relative positions of other apparatus components, such as the filter module 500. The hollow body 200 preferably has a substantially constant cross section along its length, but can alternatively have a variable cross section. The hollow body 200 preferably has a circular cross section, but can alternatively have an ovular, rectangular, polygonal, or any other suitable cross section. In one variation of the apparatus, the hollow body 200 is a hollow cylinder. The hollow body 200 is preferably substantially rigid, and is preferably made of biocompatible materials. The hollow body 200 can additionally include a coating on the hollow body interior, wherein the coating is preferably a biocompatible coating, more preferably an anticoagulant coating.

The hollow body 200 can additionally include a piston retention element, which functions to prevent complete piston removal from the hollow body. The position of the piston retention element within the hollow body can additionally function to define the second position 20. The piston retention element is preferably located along the hollow body 200 length, more preferably distal the filter module position. The piston retention element is preferably operable between a retention mode, wherein the piston retention element retains the piston head within the hollow body, and a release mode wherein the piston retention element allows complete piston head retraction from the hollow body (e.g. to allow for disassembly and sterilization). In one variation, the apparatus includes one or more through holes and one or more corresponding pins as the piston retention element, wherein the pins extend through the through holes to block piston head retraction past the pins. The pins can be removably coupled to the through-holes to allow apparatus disassembly. However, any other suitable piston retention element can be used.

The hollow body 200 can additionally define a filter retention area including a series of grooves in which the filter module 500 sits. The filter retention area is preferably located on the end of the hollow body 200 proximal the reservoir 320, but can alternatively be located in any suitable position. The hollow body 200 can also define a piston 400 arrest distal the inlet 300, wherein the piston 400 arrest preferably defines the maximum distance that the piston 400 can travel away from the inlet 300.

As shown in FIG. 1, the inlet 300 of the apparatus functions to facilitate blood ingress into the hollow body 200. The inlet 300 can additionally filter out large blood clots. The inlet 300 is preferably connected to an end of the hollow body 200, more preferably concentric with the hollow body 200, but can alternatively be coupled to any suitable portion of the hollow body 200. The inlet 300 is preferably a nozzle defining a straight channel to the volume defined by the inlet 300. However, the nozzle can alternatively define a tapering channel, a swirl channel, or any other suitable channel leading to the volume defined by the inlet 300. The nozzle preferably has a flat tip, but can alternatively have an angled tip, a threaded tip, a barbed tip, or any other suitable tip. However, the inlet 300 can be any other suitable fluid inlet 300. The inlet 300 can additionally be configured to minimize clotting during blood ingress. In one example of the apparatus, the ratio between the cross sectional areas of the inlet 300 and the hollow body 200 is configured such that the maximum negative pressure within the hollow body 200 does not exceed 150 millimeters of mercury during the intake stroke. The inlet 300 is preferably removably coupled to the hollow body 200, but can be formed as a singular piece with the hollow body 200. The inlet 300 can additionally include features for component attachment, such as barbs or threading. Components that can be attached to the inlet 300 include a needle, an IV tube, a blood bag, or any other suitable component.

Figure 4:
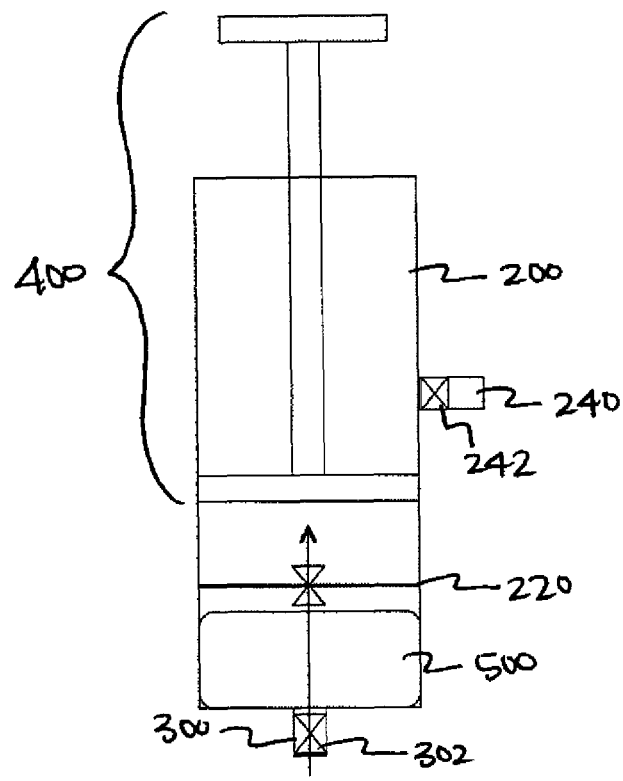
FIG. 4 is a schematic representation of a variation of the apparatus with a body valve, inlet valve, outlet, and outlet valve.
Figure 5:
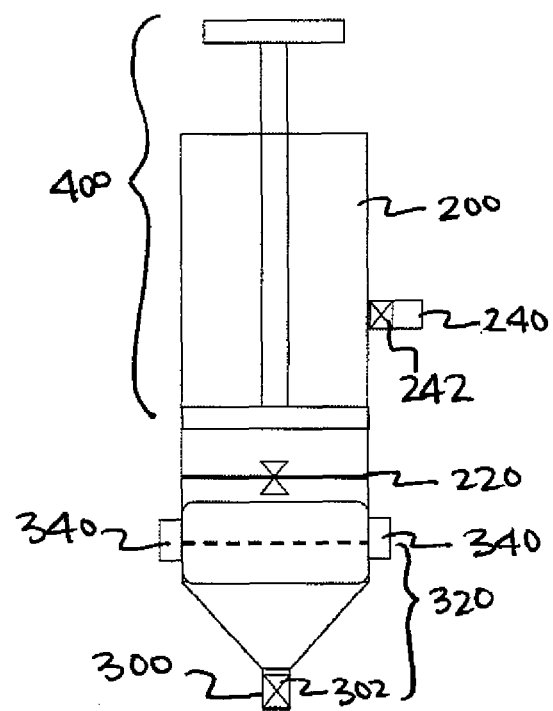
FIG. 5 is a schematic representation of a variation of the apparatus with an inlet coupling mechanism.

As shown in FIGS. 4 and 5, the inlet 300 can additionally include an inlet valve 302 between the inlet 300 and the body. The inlet valve 302 is preferably in an open position when the hollow body volume is under negative pressure, and in an open position when the hollow body volume is under positive pressure and/or at ambient pressure (e.g. atmospheric pressure). The inlet valve 302 is preferably a passive, one-way valve, but can alternatively be an active valve, a multi-way valve, or any other suitable valve. Example inlet valves 302 include a duckbill valve, a switch valve, a ball valve, or any other suitable valve.

As shown in FIG. 1, the piston 400 of the apparatus functions to generate negative pressure with the hollow body 200. As shown in FIG. 2, the piston 400 preferably includes a piston head 420, a shaft 440, and a handle 460, wherein the handle 460 preferably transfers an applied force to the piston head 420 through the shaft 440. The piston head 420 preferably has a substantially similar cross section to the hollow body interior, such that the piston head 420 perimeter forms a slidable seal with the hollow body interior. The piston head 420 is preferably made of a flexible material, such as rubber, but may be made of any suitable material that forms a substantially airtight seal against the hollow body interior. The shaft 440 preferably has a cross-like cross section, but can be a solid rod, hollow rod, or any other suitable form factor. The handle 460 is preferably a T-shaped handle 460, but can alternatively be a knob, bridge, or any other suitable handle 460.

In one variation of the apparatus, the shaft 440 and handle 460 are removably coupled to the piston head 420. This can enable the filtered blood to be stored within the apparatus, instead having to be egressed into a blood bag for long-term storage. The pressure balance between the hollow body volume and the ambient environment preferably maintains the piston head 420 position when the shaft 440 and handle 460 are removed, but the apparatus can additionally include a locking mechanism that retains the piston head 420 position. In one alternative of the apparatus, the piston head 420 and shaft 440 are threaded such that rotation of the shaft 440 about its longitudinal axis removes the shaft 440 from the piston head 420. In this alternative, the hollow body interior and the piston head 420 perimeter can additionally include complimentary threading (e.g. substantially near the second position 20), wherein rotation of the shaft 440 about its longitudinal axis rotates the piston head 420 within the hollow body 200 to lock in the piston head 420 position. Further rotation, preferably in the same direction, decouples the shaft 440 from the piston head 420. In another alternative of the apparatus, the piston head 420 and shaft 440 include a pin locking mechanism, wherein a portion of the shaft 440 can be depressed to release the shaft 440 from the piston head 420. However, any other suitable coupling mechanism can be used to couple the piston head 420 and shaft 440.

As shown in FIG. 1, the filter module 500 of the apparatus functions to separate blood clots from the blood volume, wherein blood is preferably drawn across the filter module 500 before entering the hollow body volume during the intake stroke. The filter module 500 is preferably arranged within the hollow body 200, and preferably extends across a cross section of the hollow body 200. However, the filter module 500 can alternatively be partially or wholly located within the reservoir 320. The filter module 500 is preferably cylindrical (e.g. disc-shaped) with a diameter substantially equivalent to the hollow body interior diameter, but can alternatively be conical; in one variation, the filter can substantially fill the reservoir volume. However, the filter module 500 can have any suitable shape. The filter module 500 is preferably assembled such that it is concentric with the hollow body 200, but can be assembled in any suitable position relative to the hollow body 200. The filter module 500 is preferably coupled to the hollow body 200, more preferably coupled within the hollow body 200 (e.g. within a filter module slot). However, the filter module 500 can be coupled to the reservoir 320 (e.g. within a filter module slot). In the variation wherein the reservoir 320 is removably attached to the hollow body 200, removal of the reservoir 320 preferably simultaneously removes the filter module 500 as well.

The filter module 500 preferably includes at least one filter. The pore size of the filter is preferably large enough to allow blood cells (e.g. erythrocytes) to pass through the filter, and is preferably small enough to filter out clots. The pore size is preferably no more than 170 μm (diameter), more preferably between 40 μm to 170 μm, but can alternatively be larger or smaller. The pore size can be selected based upon the application (e.g. dependent on the species from which the blood originated). The pore size is preferably substantially uniform throughout the filter, but can alternatively uniformly or non-uniformly vary throughout the filter. The filter preferably has 50% porosity, but can have any suitable porosity between 0% and 100%. The filter is preferably made of a biocompatible material, such as nylon or polyester, but can be alternatively and/or additionally be made of cloth, paper, ceramic, coated polymers, coated metals, or any other suitable material. The filter is preferably a substantially uniform, singular piece, but can be made of multiple pleated filters extending radially from the central axis of the hollow body 200. The filter is preferably a disc or block, but can alternatively be a membrane. The filter module 500 can include any suitable number of filters with any suitable pore size, wherein the filters with larger pore sizes are preferably disposed proximal the inlet 300, and the filters with smaller pore sizes are preferably disposed distal the inlet 300. In apparatus variations with multiple filters, the filters are preferably adjoined (e.g. touching the adjacent filter), but can alternatively be separated from the adjacent filter by a given distance.

In one variation of the apparatus, the filter module 500 includes at least two filters with different pore sizes. The fine filter preferably has a pore size of less than 170 μm, more preferably between 40 μm and 170 μm, and is preferably positioned proximal the piston 400. The coarse filter preferably has a pore size larger than the fine filter, and is preferably located closer proximal the inlet 300, thereby acting as a pre-filter. By removing larger clots before they can engage with the smaller pores of the fine filter, the coarse filter can increase the longevity of the original filter by preventing the fine filter from becoming clogged with the larger clots. The coarse filter preferably has a pore size no more than 170 μm (e.g. 80 μm, 100 μm, 150 μm, etc), but can alternatively have a pore size that is larger (e.g. 200 μm, 600 μm, 0.1 mm, etc.). The coarse filter is preferably adjoined to the fine filter, but can alternatively be retained a distance away from the fine filter. In one alternative of the apparatus, both the coarse filter and the fine filter are discs of substantially the same diameter. In another alternative of the apparatus, the coarse filter is conical while the fine filter is substantially frustroconical, wherein the coarse filter base is substantially the diameter of smaller base of the fine filter, and the combined filter module 500 fits within the interior volume of the reservoir 320.

In another variation of the apparatus, the filter module 500 includes a filter cartridge, wherein one or more filters are included within the filter cartridge. The filter cartridge can be removably coupled to the hollow body 200 or the reservoir 320. The filter cartridge is preferably substantially open on the ends normal to the inlet 300, such that the cartridge does not substantially impede fluid flow therethrough. The hollow body 200 preferably includes a filter cartridge slot that the filter cartridge is configured to fit within. The filter cartridge can be placed in or removed from the filter cartridge slot. The filter cartridge and filter cartridge slot preferably forms a seal therebetween, such that blood flows substantially through the filter, and does not leak through the perimeter of the filter cartridge. The filter cartridge can additionally include an O-ring between the filter cartridge and filter cartridge slot to facilitate a sufficient seal.

As shown in FIGS. 4 and 5, the apparatus preferably additionally includes a body valve 220 that permits fluid ingress into the hollow body 200 through the reservoir 320, and prevents fluid egress through the hollow body-reservoir junction. The body valve 220 preferably extends across the cross section of the hollow body 200, such that the body valve 220 can form a substantially fluid-impermeable seal against the walls of the hollow body interior. The body valve 220 is preferably located within the hollow body 200, between the filter module 500 and the piston 400. The general body valve 220 location is preferably maintained substantially static relative to the filter module 500 by the hollow body 200. For example, the body valve 220 can rest within a groove defined on the interior wall of the hollow body 200. The body valve 220 is preferably a passive, one-way valve, but can alternatively be an active valve (e.g. electrically driven), a two-way valve, or any other suitable valve. Examples of body valve 220S include switch check valves, duckbill valves, ball valves, or any other suitable valve. The body valve 220 is preferably in an open position during the intake stroke, when negative pressure is applied to the hollow body interior. The body valve 220 is preferably in a closed position during the compression stroke, when positive pressure is applied to the hollow body interior, or when the hollow body interior pressure is substantially equal to the pressure of the ambient environment (e.g. when the piston 400 is at rest relative to the hollow body 200). By maintaining a closed position during the compression stroke, as shown in FIG. 6, the body valve 220 can facilitate positive pressure generation within the hollow body volume, thus facilitating blood flow out of the hollow body 200. Alternatively, the body valve 220 can be in an open position during the compression stroke, when positive pressure is applied to the hollow body interior, wherein the blood within the hollow body 200 is egressed through the inlet 300. In another variation of the apparatus, the body valve 220 moves between the closed state to the open state during the intake stroke, and moves from the open state to the closed state during the compression stroke. However, the body valve 220 can have any other suitable configuration.

As shown in FIGS. 4 and 5, the apparatus can additionally include an outlet 240 that functions to egress blood from the hollow body 200. As shown in FIG. 6, the outlet 240 preferably provides a second fluid path for fluid egress that is different from the path of fluid ingress/fluid filtration. The outlet 240 preferably permits fluid egress from the hollow body 200 during the compression stroke, when positive pressure is applied to the hollow body interior. The outlet 240 is preferably located along the length of the hollow body 200, more preferably between the filter and the piston head 420 in the first position 10, but alternatively between the filter and the piston head 420 in the second position 20. Thus, the filtered fluid does not need to flow through the contaminated fluid to egress from the hollow body 200. The outlet 240 preferably includes an outlet barb or threading to which a blood bag, tubing, or any other suitable transfusion mechanism can be coupled. The ratio between the cross-sectional area of the outlet 240 and the hollow body 200 is preferably configured to limit the maximum positive pressure to 150 millimeters of mercury.

Figure 6A:
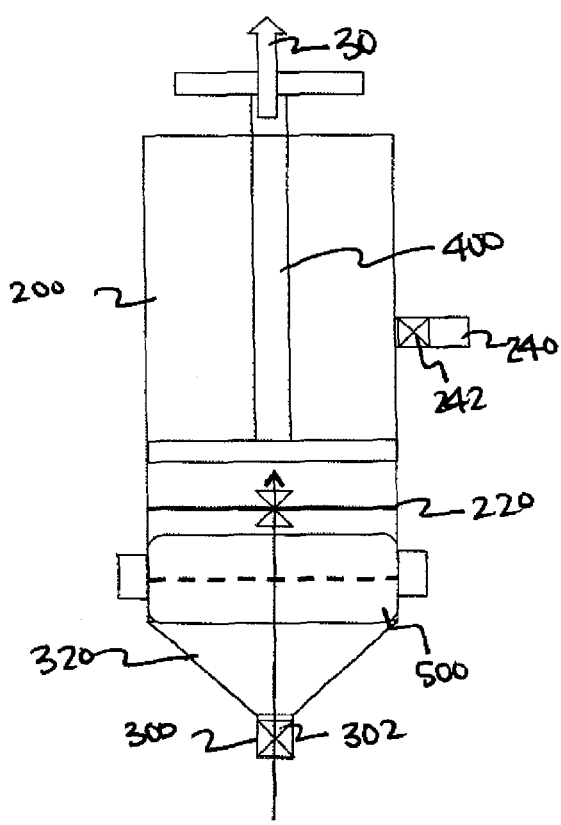
FIGS. 6A and 6B are schematic representations of operation of a variation of the apparatus through an intake stroke and a compression stroke, respectively.
Figure 6B:
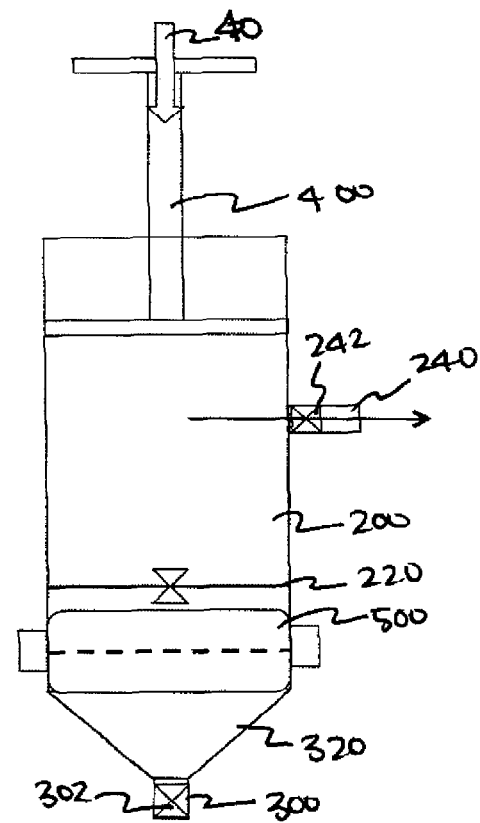

The outlet 240 can additionally include an outlet valve 242 between the outlet 240 and the body. The outlet valve 242 is preferably a passive, one-way valve, but can alternatively be an active valve, a multi-way valve, or any other suitable valve. Example outlet valves 242 include a duckbill valve, a switch valve, a ball valve, or any other suitable valve. In one variation of the apparatus, as shown in FIG. 6A, the outlet valve 242 is preferably in a closed position when the hollow body volume is under negative pressure and/or is at ambient pressure (e.g. atmospheric pressure), and in an open position when the hollow body volume is under positive pressure, as shown in FIG. 6B.

In a second variation of the apparatus, the outlet valve 242 is in an open position when the hollow body volume is under negative pressure, in an open position when the hollow body volume is under positive pressure, and is in a closed position when the hollow body volume pressure is substantially equal to the atmospheric pressure. In this variation, a blood bag containing an anticoagulant solution can be coupled to the outlet 240 prior to the intake stroke. When the piston 400 is moved through the intake stroke, blood and anticoagulant are simultaneously drawn into the hollow body volume through the inlet 300 and outlet 240, respectively, wherein the blood mixes with the anticoagulant within the hollow body volume. Translation of the piston 400 through the compression stroke then pushes the anticoagulant-blood mixture into the coupled blood transfusion device (e.g. blood bag). In this variation, the outlet 240 can additionally include a microfilter that functions to filter microorganisms and/or particulates from the anticoagulant solution prior to ingress into the hollow body volume; the microfilter is preferably removed prior to solution egress from the hollow body 200. Alternatively, coupling a blood transfusion device (e.g. a blood bag) to the outlet 240 can switch the outlet 240 from maintaining a closed position during the intake stroke to maintaining an open position during the intake stroke.

Figure 3A:
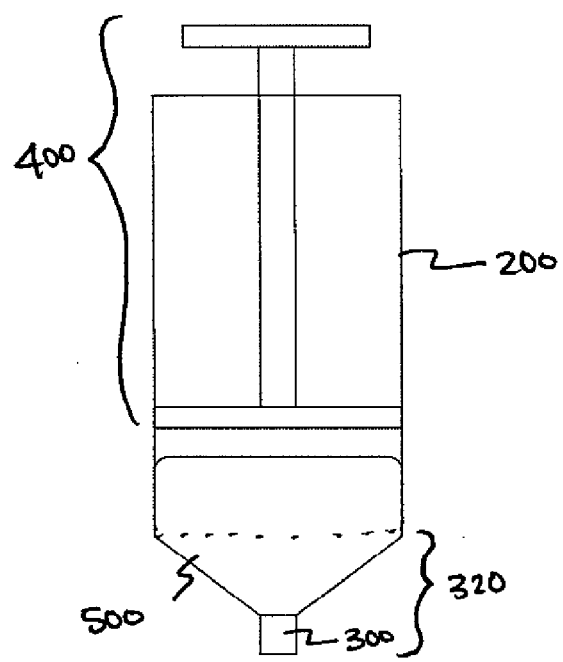
FIGS. 3A and 3B are schematic representations of a variation of the apparatus with a reservoir with a cone filter module and a disc filter module, respectively.
Figure 3B:
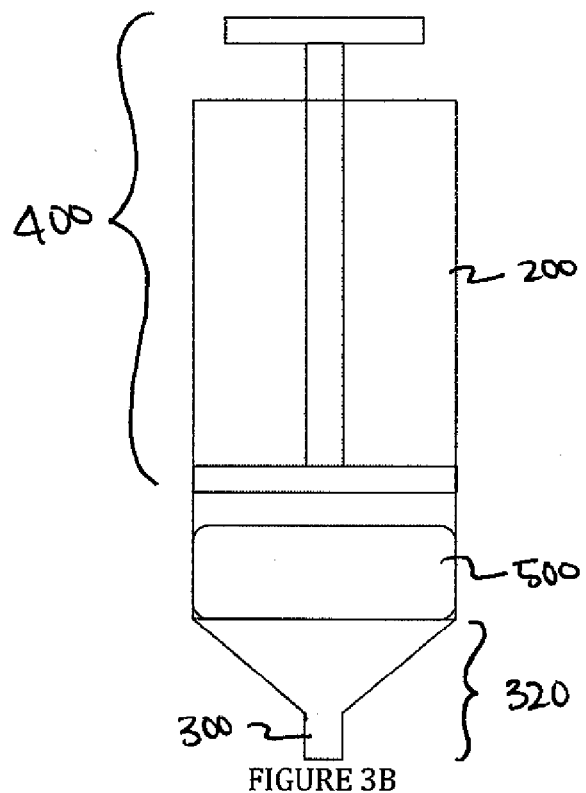

As shown in FIGS. 3 and 5, the apparatus can additionally include a reservoir 320 that couples the inlet 300 to the hollow body 200. The reservoir 320 is preferably substantially hollow, and defines a reservoir volume. The reservoir configuration preferably minimizes blood clot formation, and preferably promotes laminar flow and/or minimize turbulent flow between the inlet 300 and the hollow body 200. The reservoir 320 preferably provides a smooth transition between the inlet 300 and the hollow body 200. The reservoir 320 can additionally provide a region for liquid and clotted blood to enter the device with sufficient volume for the liquid blood to separate from the solid clots and enter the filter. The reservoir 320 then acts as a storage area for the clots that cannot pass through the filter. The reservoir 320 is preferably substantially unoccupied by other apparatus components, as shown in FIG. 3B, but can alternatively be partially or wholly occupied by the filter module 500 (e.g. when the filter module 500 is conical), as shown in FIG. 3A.

In one variation of the apparatus, the reservoir 320 is conical, wherein the inlet 300 is located at the tip of the conical reservoir 320, and the hollow body 200 couples to the base of the conical reservoir 320. The reservoir 320 can be a parabolic cone, an elliptical cone, a frustum, a cylinder, or any other suitable shape, wherein the inlet 300 is preferably located on at the reservoir apex, concentric with the reservoir central axis, but can alternatively be located in any other suitable position. The reservoir 320 and inlet 300 are preferably manufactured as a singular piece, but can alternatively be manufactured as separate pieces.

The apparatus can additionally include an inlet coupling mechanism 340 that removably couples the inlet 300 to the hollow body 200. More preferably, the inlet coupling mechanism 340 removably couples the reservoir 320 to the hollow body 200. The inlet coupling mechanism 340 preferably enables the apparatus to be operable between an open and closed configuration. In the open configuration, the reservoir 320 is preferably at least partially decoupled from the hollow body 200 such that the filter module 500 can be accessed. More preferably, the filter module 500 can be removed from the apparatus when the apparatus is in the open configuration. The body valve 220 preferably seals the hollow body volume in the open configuration. In the closed configuration, the reservoir perimeter preferably forms a fluid impermeable seal with the hollow body perimeter. The reservoir-hollow body junction can additionally include an O-ring or gasket to facilitate a better fluid seal. By allowing the apparatus to be opened, the inlet coupling mechanism 340 can allow for apparatus disassembly, which can facilitate apparatus component sterilization (e.g. autoclaving) and apparatus reuse.

In one variation of the apparatus, the inlet coupling mechanism 340 includes at least two connecting mechanisms, wherein the connecting mechanisms are preferably evenly distributed about the reservoir 320 and hollow body 200 perimeters. The connecting mechanism can be a latch, clip, bayonet locking mechanism, screw, adhesive, or any other suitable connecting mechanism. In another variation of the apparatus, the inlet coupling mechanism 340 includes a hinge rotatably connecting the hollow body 200 and reservoir 320 and a connecting mechanism, wherein the connecting mechanism and hinge cooperatively seal the reservoir 320 against the hollow body 200 when the connecting mechanism is engaged. However, the inlet coupling mechanism 340 can include clips, screws, adhesive, a spring-force mechanisms (e.g. a rubber band that is stretched between the reservoir 320 and the hollow body 200 distal the reservoir 320), or any other suitable coupling mechanism.

The apparatus can additionally include a volume of anticoagulant solution, preferably located within the hollow body 200, wherein blood can mix with the anticoagulant solution upon ingress into the hollow body volume. The anticoagulant solution can include one or more antithrombotics, such as heparin or coumarin compounds, one or more thrombolytics, such as streptokinase or urokinase, and/or one or more antithrombocytics. The anticoagulant volume within the hollow body 200 is preferably less than the maximum hollow body volume, achieved when the piston head 420 is in the second position 20. More preferably, the anticoagulant volume is less than half the maximum hollow body volume. Alternatively, any suitable volume of anticoagulant solution can be included, wherein the anticoagulant volume is preferably determined based on the concentration of the anticoagulant solution.

The components of the apparatus are preferably made of materials that can withstand sterilization processes, such as heat sterilization, radiation sterilization, or chemical sterilization. Example sterilization processes include autoclaving, UV light exposure, or bleaching. Furthermore, the apparatus components are preferably made of one or more biocompatible materials, more preferably bioinert materials. Example materials include Topas-Cyclic Olefin Copolymers (TCOC), Makrolon® (Bayer MaterialScience), polycarbonate, polyethylene terephthalate (PET), polytetrafluoroethylene (PTFE), polyethylene, polymethylmethacrylate (PMA), biocompatible polymers, biocompatible ceramics, and biocompatible metals, such as titanium, stainless steel. However, the apparatus components can be made of any suitable material. The apparatus components can additionally include a coating. In one variation of the apparatus, the coating can decrease blood clotting. In another variation of the apparatus, the coating is a biocompatible coating; this can be desirable if the apparatus component is made of a biologically incompatible material. The coating can include silicone, an anticoagulant coating (e.g. EDTA, citrate, oxlate, etc.), or any other suitable coating. The apparatus components are preferably injection molded, but can alternatively be sintered, stamped, or manufactured using any other suitable method.

In one variation, the apparatus includes a hollow body 200, a reservoir 320 with an inlet 300 connected to a hollow body 200 end, a piston 400 slidably disposed within the hollow body 200, and a filter module 500 within the hollow body 200 between the piston 400 and the inlet 300, and a body valve 220 within the hollow body 200 between the filter and the piston 400. The hollow body 200 further includes outlet 240, and an outlet valve 242, and the reservoir 320 further includes an inlet valve 302. The reservoir 320 and hollow body 200 are removably coupled by a bayonet locking mechanism. The piston 400 includes a piston head 420 with substantially the same diameter as the inner diameter of the hollow body 200, a shaft 440 coupled to the piston head 420, and a handle 460 coupled to the shaft 440.

In one alternative of the apparatus, movement of the piston 400 through the inlet 300 stroke opens the inlet 300 and body valve 220S and draws fluid (e.g. blood) through the filter into the hollow body 200. Movement of the piston 400 through the compression stroke opens the outlet valve 242 and egresses fluid through the outlet 240. In this variation, a blood bag or transfusion tube is preferably coupled to the outlet valve 242 prior to blood egress. The valves are preferably all closed when the piston 400 is not translating.

In another alternative of the apparatus, movement of the piston 400 through the intake stroke opens the inlet valve 302, body valve 220, and outlet valve 242, simultaneously drawing blood and fluid (e.g. anticoagulant solution) from the blood source (e.g. patient or collection volume) and coupled blood bag, respectively. Movement of the piston 400 through the compression stroke closes the inlet valve 302 and body valve 220 and opens the outlet valve 242, allowing blood egress out of the outlet 240 into the blood bag.

In another alternative of the apparatus, movement of the piston 400 through the intake stroke opens the inlet valve 302 and the body valve 220, and draws blood through the filter into the hollow body volume. The piston 400 position is retained by the substantially equal force between the hollow body volume and the ambient environment. All valves are preferably closed when the piston 400 position is maintained. The reservoir 320 is decoupled from the hollow body 200 and the filter module 500 removed; the closed body valve 220 preferably maintains the hollow body volume sterility and pressure during this process. The reservoir 320 is then re-coupled to the hollow body 200, and movement of the piston 400 through the compression stroke opens the body valve 220 and egresses blood through the inlet 300. The original reservoir 320 can be used, a new filter module 500 can be installed, or a new reservoir 320 can be used for blood egress from the hollow body volume. This alternative can additionally include decoupling the piston 400 shaft 440 and handle 460 from the piston head 420 to retain the piston 400 position.

As a person skilled in the art will recognize from the previous detailed description and from the figures and claims, modifications and changes can be made to the preferred embodiments of the invention without departing from the scope of this invention defined in the following claims.

We claim:

1. A blood filtering apparatus comprising:
   a hollow body defining an interior volume;
   an inlet fluidly coupled to the hollow body;
   a piston slidably engaged within the hollow body;
   a filter arranged across a hollow body cross section between the inlet and piston;
   a body valve arranged across a second hollow body cross section, between the filter and the piston, wherein the body valve is operable between an open configuration and a closed configuration; and
   a reservoir fluidly coupled to the hollow body and positioned between the inlet and the filter;
   wherein the piston and hollow body cooperatively generate a negative pressure, relative to ambient, within the hollow body during piston translation from a first proximal position to a second more distal position, and cooperatively generate a positive pressure, relative to ambient, within the hollow body during piston translation from the second position to the first position;
   wherein the hollow body and the inlet are configured such that a ratio between a cross-section of the hollow body and a cross-section of the inlet limits a maximum negative pressure generated within the interior volume to no greater than 150 mm Hg;
   wherein the reservoir is conically shaped to minimize turbulent flow of blood between the inlet and the hollow body; and
   wherein the body valve is in the open configuration when the hollow body is under negative pressure, and is in the closed configuration when the hollow body is under positive pressure.

2. The apparatus of claim 1, wherein the apparatus further comprises an outlet disposed along the hollow body length, between the body valve and the second position.

3. The apparatus of claim 2, wherein the outlet comprises an outlet valve operable between a closed position when the hollow body is under negative pressure; and an open position when the hollow body is under positive pressure.

4. The apparatus of claim 2, wherein the outlet is arranged proximal the body valve.

5. The apparatus of claim 1, wherein the inlet is concentrically located at an apex of the conical reservoir.

6. The apparatus of claim 5, wherein the filter is conical, and substantially occupies the reservoir.

7. The apparatus of claim 1, wherein the filter comprises a coarse filter and a fine filter, the coarse filter having a larger pore size than the fine filter, wherein the coarse filter is arranged proximal the inlet and the fine filter is arranged distal the inlet.

8. The apparatus of claim 7, wherein the fine filter has a pore size of no more than 170 micrometers.

9. The apparatus of claim 1 further comprising a coupling mechanism removably coupling the inlet to the hollow body.

10. The apparatus of claim 9, wherein the coupling mechanism comprises a bayonet locking mechanism.

11. A blood filtering apparatus comprising:
    a cylindrical hollow body;
    an inlet fluidly coupled to an end of the hollow body;
    a piston slidably engaged within the hollow body, the piston operable between: an intake stroke, wherein the piston applies a negative pressure, relative to ambient, to the hollow body interior; and a compression stroke, wherein the piston applies a positive pressure, relative to ambient, to the hollow body interior;
    a filter removably coupled within the hollow body between the inlet and piston, the filter having a pore size of no more than 170 micrometers;
    a body valve located within the hollow body, between the filter and the piston, wherein the body valve is operable between an open configuration during the intake stroke and a closed configuration during the compression stroke;
    an outlet disposed along the hollow body length between the body valve and the piston;

an outlet valve disposed within the outlet, operable between an open configuration during the compression stroke and a closed configuration during the intake stroke;

a conical reservoir fluidly coupled between the inlet and the hollow body and configured to minimize turbulent flow of blood between the inlet and the hollow body, wherein the inlet is disposed at an apex of the reservoir, and wherein a base of the reservoir connected, and equal in diameter, to the hollow body; and, an inlet coupling mechanism removably coupling the reservoir to the hollow body, wherein the hollow body and the inlet are configured such that a ratio between a cross-section of the hollow body and a cross-section of the inlet limits a maximum negative pressure generated within the interior volume to no greater than 150 mm Hg.

12. The apparatus of claim 11, wherein the inlet further comprises an inlet valve operable between an open configuration during the intake stroke and a closed configuration during the compression stroke.

13. The apparatus of claim 12, wherein the body valve, outlet valve, and inlet valve are passive, one-way check valves.

14. The apparatus of claim 11, wherein the inlet coupling mechanism comprises a bayonet locking mechanism.

15. The apparatus of claim 11, further comprising a second filter removably coupled within the hollow body between the inlet and first filter, the second filter having a pore size larger than the first filter.

16. The apparatus of claim 15, further comprising a filter cartridge coupling the first and second filters together, wherein the filter cartridge is removably coupled to the hollow body.

17. The apparatus of claim 11, wherein the inlet and reservoir are a singular piece.

18. The apparatus of claim 11, wherein the piston comprises a piston head, a shaft, and a handle, and wherein the shaft and the handle are removably coupled to the piston head.

19. A blood filtering and collection system comprising: the apparatus of claim 11, wherein the outlet is coupleable to a blood transfusion device; and the blood transfusion device.

20. The system of claim 19, further comprising a volume of anticoagulant solution configured to mix with blood within the hollow body.

* * * * *